US009155866B2

(12) United States Patent
Bornhoft (10) Patent No.: US 9,155,866 B2
(45) Date of Patent: Oct. 13, 2015

(54) LUER SECUREMENT DEVICE

(75) Inventor: Stephen Bornhoft, Midvale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 324 days.

(21) Appl. No.: 13/614,481

(22) Filed: Sep. 13, 2012

(65) Prior Publication Data

US 2014/0074037 A1   Mar. 13, 2014

(51) Int. Cl.
*A61M 25/02* (2006.01)
*A61M 39/06* (2006.01)
*A61M 39/02* (2006.01)
*A61M 5/158* (2006.01)

(52) U.S. Cl.
CPC ....... *A61M 25/02* (2013.01); *A61M 2005/1586* (2013.01); *A61M 2005/1587* (2013.01); *A61M 2025/028* (2013.01); *A61M 2025/0253* (2013.01); *A61M 2039/0279* (2013.01); *A61M 2039/0633* (2013.01)

(58) Field of Classification Search
CPC . A61M 39/02; A61M 39/0247; A61M 39/06; A61M 2039/027; A61M 2039/0279; A61M 2039/0633; A61M 2039/0634; A61M 2039/0653; A61M 2039/066
USPC ............... 604/93.01, 164.01, 167.01, 167.02, 604/167.03, 167.04, 167.06, 174, 175, 180
See application file for complete search history.

(56) References Cited

U.S. PATENT DOCUMENTS

| | | | | |
|---|---|---|---|---|
| 2,402,306 | A * | 6/1946 | Turkel | ............................ 604/174 |
| 4,004,298 | A * | 1/1977 | Freed | ............................ 623/3.1 |
| 4,488,545 | A | 12/1984 | Shen | |
| 4,581,020 | A * | 4/1986 | Mittleman | ..................... 604/175 |
| 4,645,492 | A * | 2/1987 | Weeks | ........................... 604/174 |
| 4,755,173 | A * | 7/1988 | Konopka et al. | ......... 604/167.02 |
| 5,251,873 | A * | 10/1993 | Atkinson et al. | ............ 251/149.1 |
| 5,531,720 | A | 7/1996 | Atkins | |
| 5,632,729 | A * | 5/1997 | Cai et al. | .................. 604/288.01 |
| 5,833,213 | A | 11/1998 | Ryan | |
| 6,461,329 | B1 * | 10/2002 | Van Antwerp et al. | ....... 604/111 |
| 7,455,663 | B2 | 11/2008 | Bikovsky | |
| 7,666,166 | B1 | 2/2010 | Emmert et al. | |
| 2002/0161332 | A1 | 10/2002 | Ramey | |
| 2002/0173769 | A1 * | 11/2002 | Gray et al. | ..................... 604/506 |
| 2003/0229308 | A1 * | 12/2003 | Tsals et al. | ..................... 604/116 |
| 2004/0204685 | A1 * | 10/2004 | Wright et al. | ................. 604/174 |
| 2007/0185441 | A1 | 8/2007 | Fangrow, Jr. | |
| 2008/0154205 | A1 | 6/2008 | Wojcik | |
| 2010/0204675 | A1 | 8/2010 | Woehr et al. | |
| 2011/0160662 | A1 | 6/2011 | Stout et al. | |
| 2012/0197204 | A1 * | 8/2012 | Helm, Jr. | ....................... 604/176 |
| 2012/0226239 | A1 | 9/2012 | Green | |

FOREIGN PATENT DOCUMENTS

| | | |
|---|---|---|
| EP | 1 776 980 A1 | 4/2007 |
| EP | 2 364 738 A2 | 9/2011 |
| EP | 2 399 624 A1 | 12/2011 |
| EP | 2 433 663 A1 | 3/2012 |
| WO | 2006/062636 A1 | 6/2006 |
| WO | 2008/133702 A1 | 11/2008 |
| WO | 2011/089193 A2 | 7/2011 |
| WO | 2011/121023 A1 | 10/2011 |

* cited by examiner

*Primary Examiner* — Aarti B Berdichevsky
*Assistant Examiner* — Nilay Shah
(74) *Attorney, Agent, or Firm* — Jeanne Lukasavage; Craig Metcalf; Kirton McConkie (57) ABSTRACT

A Luer securement device comprising a flexible hood that is configured to attach to the surface of a patient, the flexible hood further having a Luer adapter for receiving a catheter inserter and/or a fluid line. The Luer securement device further includes a wedge seal that is positioned within the Luer adapter and is configured to receive a base portion of a catheter during a catheterization procedure. Once the base of the catheter is seated within the wedge seal, a proper insertion depth of the catheter into the patient is achieved.

20 Claims, 8 Drawing Sheets

LUER SECUREMENT DEVICE

BACKGROUND OF THE INVENTION

This disclosure relates generally to catheters and Luer devices. More specifically, this disclosure discusses a Luer securement device that comprises a flexible hood coupled to a Luer adapter having a wedge seal disposed therein, wherein the flexible hood is attached to a patient and a catheter is simultaneously inserted into the patient and seated within the wedge seal during a catheterization procedure.

As used herein, the term "Luer" is understood to describe and include any Luer taper or other system of small-scale fluid fittings used for making leak-free connections between a male-taper fitting and its mating female part on medical devices and/or equipment. A Luer device in accordance with the present invention may further include an integrated septum, whereby to provide selective access between two devices interconnected via a Luer fitting connection. Non-limiting examples of Luer fittings include "Luer-Lok," "Luer-Slip," and "Nexiva Closed IV Catheter" systems produced by Becton Dickenson, Inc.

Infusion therapy involves the administration of a fluid to a patient through a needle or catheter. It is generally prescribed when a patient's treatment cannot be treated effectively by oral medication. Typically, "infusion therapy" refers to procedures where a drug or other fluid is administered intravenously. However, the term also refers to situations where fluids are provided through other non-oral routes, such as intramuscular injections, subcutaneous injections, and epidural routes.

Infusion therapies are generally used to introduce to or remove fluid from a patient. The infusion process generally requires steady control of the catheter and needle to ensure proper access while avoiding or minimizing injury to the patient. In emergency situations, such as in the back of a moving ambulance, a physician or other caregiver may be incapable of inserting a catheter into a patient due to excessive movement of the patient's surrounding. As such, the ambulance is required to stop to allow the caregiver a steady environment in which to insert the catheter. This creates an inconvenience to the caregiver and wastes valuable time that may be needed to save the life of the patient. Accordingly, there is a need in the art for a device which overcomes the difficulties and shortcomings associated with currently available technologies. The present disclosure discusses such a device.

BRIEF SUMMARY OF THE INVENTION

The present invention provides a Luer securement device which includes a flexible hood having a base configured to attach to a surface of a patient, thereby forming a secure interface with the patient. The flexible hood is attached to a Luer adapter. The Luer adapter includes a wedge seal disposed on an inner surface of the Luer adapter. The Luer adapter further includes a septum disposed within the Luer adapter, an inner lumen being formed between the wedge seal and the septum.

In some instances, the Luer securement device further comprises a hood adapter having a distal end coupled to a proximal end of the flexible hood, the hood adapter further having a proximal end coupled to the Luer adapter. The base of the flexible hood may further include an adhesive film that isolates an inner or interior environment of the flexible hood from an exterior environment.

The wedge seal generally comprises an annular seal having an inner diameter configured to receive a base portion of a catheter. The base portion of the catheter is seated into the wedge seal as part of a catheterization process. In some implementations, the inner diameter of the wedge seal receives the outer surface of the base of the catheter to form a fluid tight seal.

The Luer adapter portion of the Luer securement device further comprises a set of threads to compatible receive a catheter inserter. A catheter inserter may include any device or combination of devices which deliver and insert a catheter into the Luer securement device as part of a catheterization process. For example, a catheter inserter may include a probe that contacts the base portion of the catheter to advance the catheter through the septum of the Luer adapter and into the patient such that the base portion of the catheter is seated into the wedge seal.

In some implementations, the base of the flexible hood is angled relative to a sidewall of the flexible hood to facilitate insertion of the catheter at a desired angle. For example, in some instances the base is angled from approximately 30° to approximately 90°.

The present invention further includes one or more methods for manufacturing a Luer securement device. In some implementations, a method for manufacturing a Luer securement device includes steps for 1) providing a flexible hood having a base configured to attach to a surface of a patient; 2) coupling the flexible hood to a Luer adapter; 3) inserting a wedge seal into an inner surface of the Luer adapter; and 4) disposing a septum with the Luer adapter. Method of the present invention may further include steps for providing a hood adapter, wherein the hood adapter is coupled to a proximal end of the flexible hood and a distal end of the Luer adapter. A step may further be provided for attaching an adhesive film to the base of the flexible hood, wherein the adhesive film encloses an interior environment of the flexible hood.

Some implementations of the present invention further include a Luer securement device having a flexible hood having a base configured to attach to a surface of a patient; an adhesive film attached to the base and enclosing an internal environment of the flexible hood; a Luer adapter coupled to the flexible hood, an inner surface of the Luer adapter comprising an annular wedge seal; a septum disposed within the Luer adapter; and an insertion target formed on the adhesive film and in concentric alignment with the septum and the annular wedge seal.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which:

FIG. 3, shown in parts A and B, illustrates a cross-section view of a Luer securement device prior to receiving a catheter in accordance with a representative embodiment of the present invention.

FIG. 4, shown in parts A-D, illustrates a cross-section view of a Luer securement device at various positions during a catheterization process in accordance with a representative embodiment of the present invention.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the accompanying Figures, could be arranged and designed in a wide variety of different configurations. Thus, the following more detailed description of some embodiments of the invention, as represented in the Figures, is not intended to limit the scope of the invention, as claimed, but is merely representative of some presently preferred embodiments of the invention.

Generally, the present invention relates to an integrated Luer securement device for securing a catheter and a Luer access port or coupler to a patient. In particular, some embodiments of the present invention provide a Luer securement device that is attached to a patient and subsequently receives a catheter that is inserted into the patient. The process of coupling the catheter to the Luer securement device provides an integrated unit that secures and maintains the position of the catheter within the patient. Further, the integrated device protects and shields the insertion site of the catheter, thereby preventing infection and undesirable blood exposure to a caregiver.

In some instances, the Luer securement device comprises a hood made of a flexible polymer material which comprises a base configured to form an interface with a body surface of a patient. In some embodiments, the base of the Luer adapter further comprises an adhesive to secure and fix the location of the Luer securement device on the patient. The Luer securement device further comprises a Luer adapter onto which is temporarily coupled a catheter inserter. The catheter inserter is configured to advance a catheter through the Luer securement device and into the patient. Upon completed insertion into the patient, a base portion of the catheter is seated within a wedge seal of the Luer securement device, thereby providing the integrated device. The wedge seal provides a fluid tight seal between the base of the catheter and the Luer adapter, thereby isolating the area surrounding the insertion site from an exterior environment. Following insertion of the catheter into the patient, the catheter inserter is selectively removed from the Luer adapter and discarded. The Luer adapter remains in place thereby allowing fluid access to the patient.

The embodiments of the present invention further include a catheter. The catheter of the present invention may include any type or style of catheter compatible with in vitro use. For example, in some instances the present invention includes an intravascular catheter, or a subcutaneous or intramuscular catheter. Accordingly, catheters compatible with the present invention may include flexible, polymer catheters and or rigid polymer or metallic catheters.

The catheter inserter may include any device or combination of devices to facilitate simultaneous catheterization of the patient and placement of the catheter's base into the wedge seal of the Luer securement device. Non-limiting examples of compatible catheter inserters are taught in U.S. patent application Ser. No. 13/615,201, titled INTEGRATED CATHETER SECUREMENT AND LUER ACCESS DEVICE, filed Sep. 13, 2012 by Stephen Bornhoft, and U.S. patent application Ser. No. 13/615,012, titled INTRAVENOUS CATHETER INSERTER, filed Sep. 13, 2012 by Stephen Bornhoft, each of which is incorporated herein in its entirety. In some instances a catheter inserter comprises a probe configured to advance a catheter through a septum of the Luer securement device and into a patient. The catheter inserter further includes a needle which extends through the probe of the catheter inserter and through the catheter to assist in inserting the catheter into a patient. Once the catheter is inserted into the patient, the catheter inserter and needle are retracted, and the catheter inserted is removed from the Luer securement device.

The interconnected relationship between the Luer securement device and the catheter inserter provides a bridged connection between the catheter and the surface of the patient. In particular, the hood of the Luer securement device provides a stable, constant connection between the patient and the catheter thereby permitting catheterization of a patient in unstable surroundings or conditions. In other words, the hood of the Luer adapter provides a constant connection between the Luer securement device and the surface of the patient, such that a distance between the user's hand and the patient remains constant during catheterization. To provide a better understanding of the Luer securement device, the various integrated components of the device are described below in greater detail.

Figure 1:
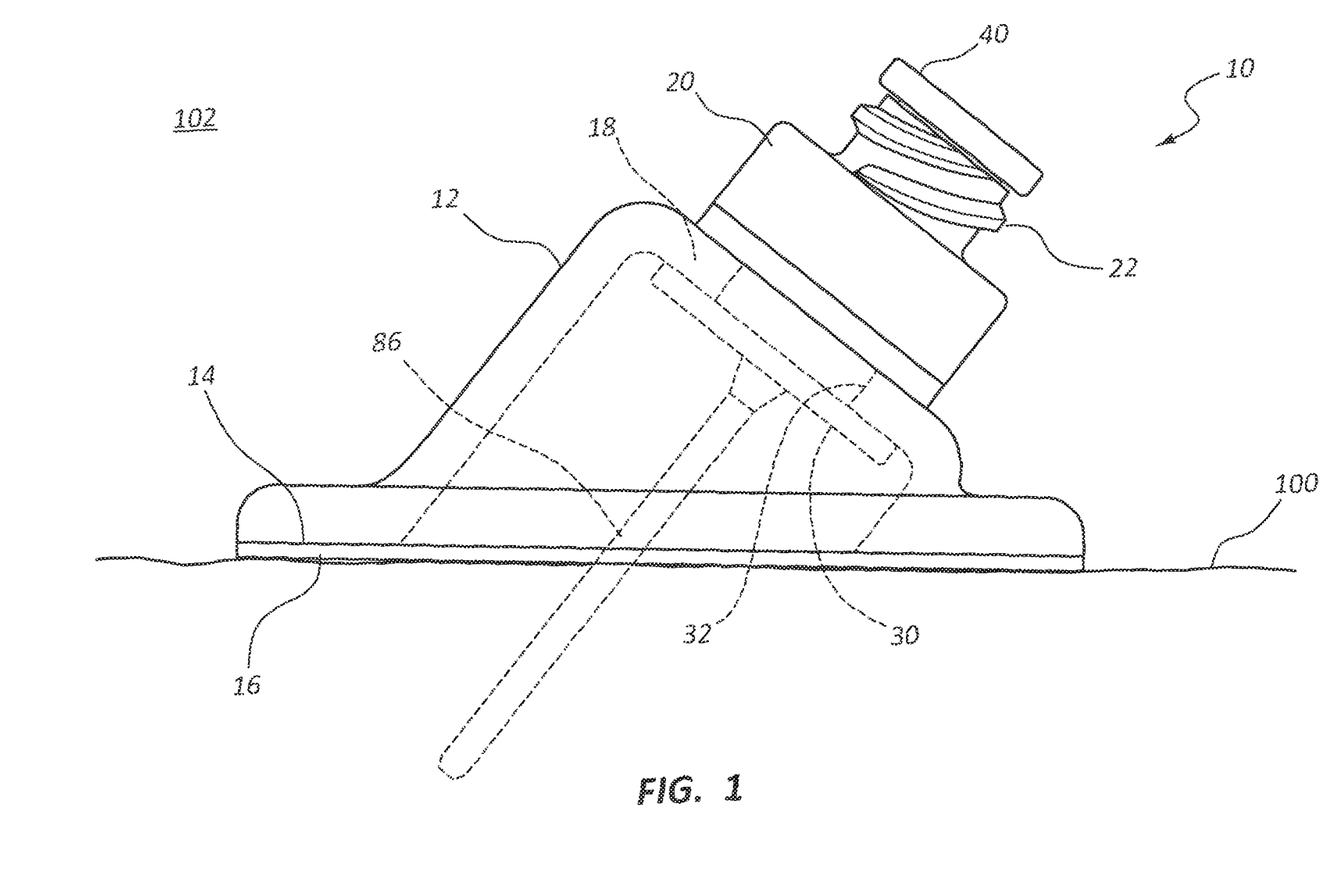
FIG. 1 illustrates a perspective side view of a Luer securement device coupled to the surface of a patient in accordance with a representative embodiment of the present invention.

Referring now to FIG. 1, a perspective view of an assembled Luer securement device 10 is shown secured to a patient 100. In general, Luer securement device 10 comprises a flexible hood 12 having a base 14 that is coupled to an adhesive layer or film 16. Adhesive film 16 is applied to patient 100 to secure and retain the position of Luer securement device 10 on patient 100. In some embodiments, the adhesive surface further comprises a protective wrap or covering 17 that is removed to expose the adhesive surface prior to applying Luer securement device 10 to the patient 100 (see FIG. 3B, for example).

Flexible hood 12 is secured to a Luer connector or adapter 20. In some embodiments, flexible hood 12 is secured to Luer adapter 20 via a hood adapter 30. For example, in some embodiments a proximal end or upper lip portion 18 of flexible hood 12 is inserted into a distal end or annular channel 32 of hood adapter 30. A proximal end of hood adapter 30 is further coupled to a distal end of Luer adapter 20. Luer adapter 20 further comprises a set of threads 22 to receive a catheter inserter and/or a fluid delivery apparatus, such as syringe or fluid line. Luer securement device 10 further comprises a septum 40 which is housed within Luer adapter 20.

Figure 2:
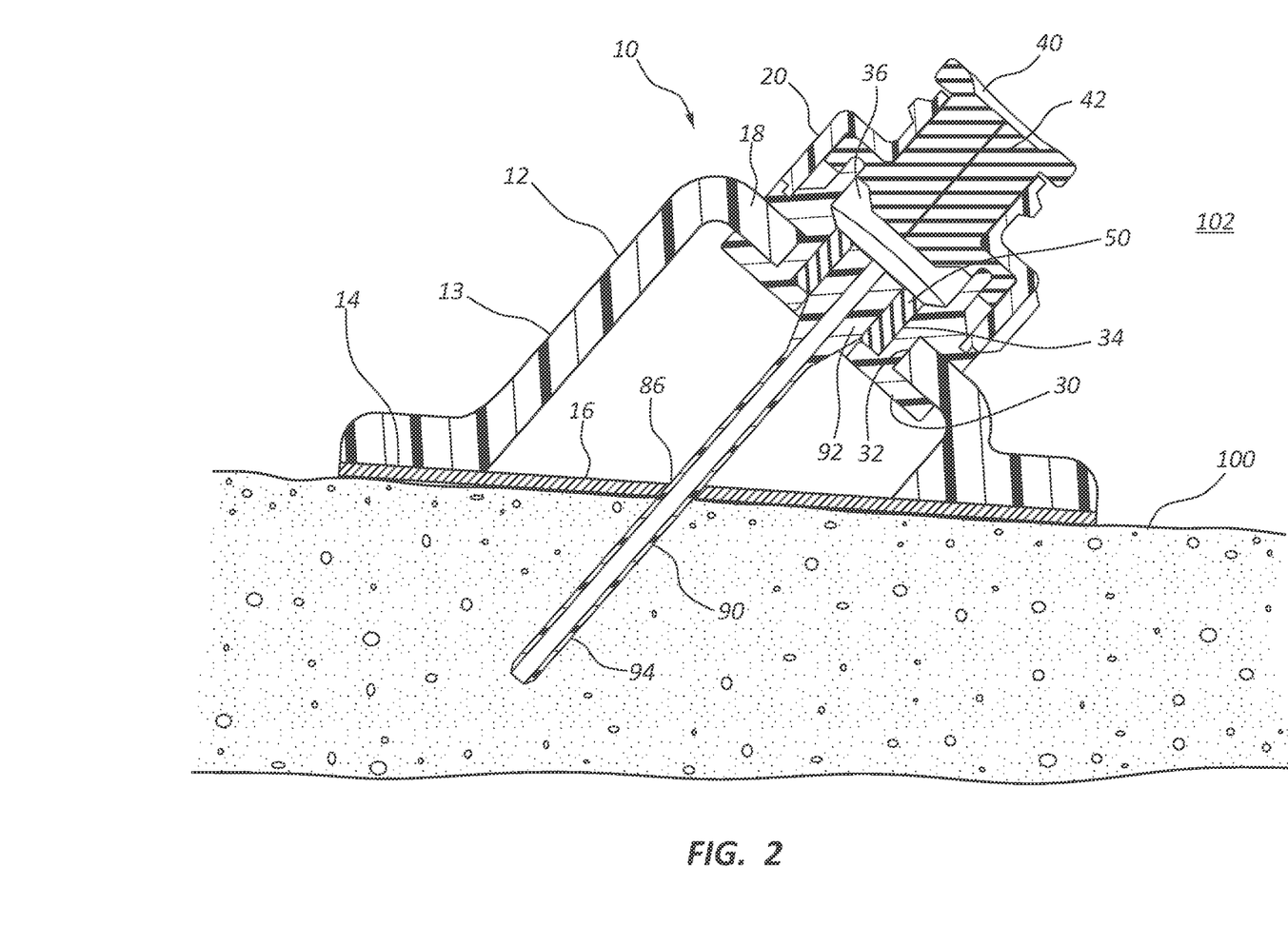
FIG. 2 illustrates a cross-section view of a Luer securement device of FIG. 1 in accordance with a representative embodiment of the present invention.

Referring now to FIG. 2, a cross-section view of Luer securement device 10 is shown. In some embodiments, septum 40 is housed within Luer adapter 20 and interlocked between Luer adapter 20 and hood adapter 30. As such, the position of septum 40 is maintained during use of device 10. Septum 40 may further include a slit 42. Slit 42 may be pre-cut or may be provided by the needle of the catheter inserter during the catheterization process. In some instances, slit 42 is self-sealing. In the closed or sealed position, septum 40 and slit 42 prevent fluid communication between insertion site 86 and exterior environment 102, thereby preventing user exposure to blood, and preserving the sterile environment within flexible hood 12.

Hood adapter 30 further comprises a wedge seal 50. Wedge seal 50 generally comprises an annular polymer seal that is seated into a channel or groove 34 formed on an interior surface of adapter 30. Wedge seal 50 further comprises an inner diameter that is configured to compatibly receive and retain a base 92 of catheter 90 in a fluid tight manner, as shown.

In some embodiments, catheter 90 is advanced through slit 42 of septum 40 and into patient 100 to a depth whereby base 92 of catheter 90 is fully seated into wedge seal 50. Accordingly, a desired depth of insertion of catheter 90 may be selected by increasing or decreasing the length between tip 94 and base 92 of catheter 90. The fully seated position of base 92 within wedge seal 50 provides a fluid tight seal that further isolates insertion site 86 from exterior environment 102. Further, the fluid tight seal between base 92 and wedge seal 50 prevent leakage of fluids between lumen 36 and the sterile environment within flexible hood 12.

Figure 3A:
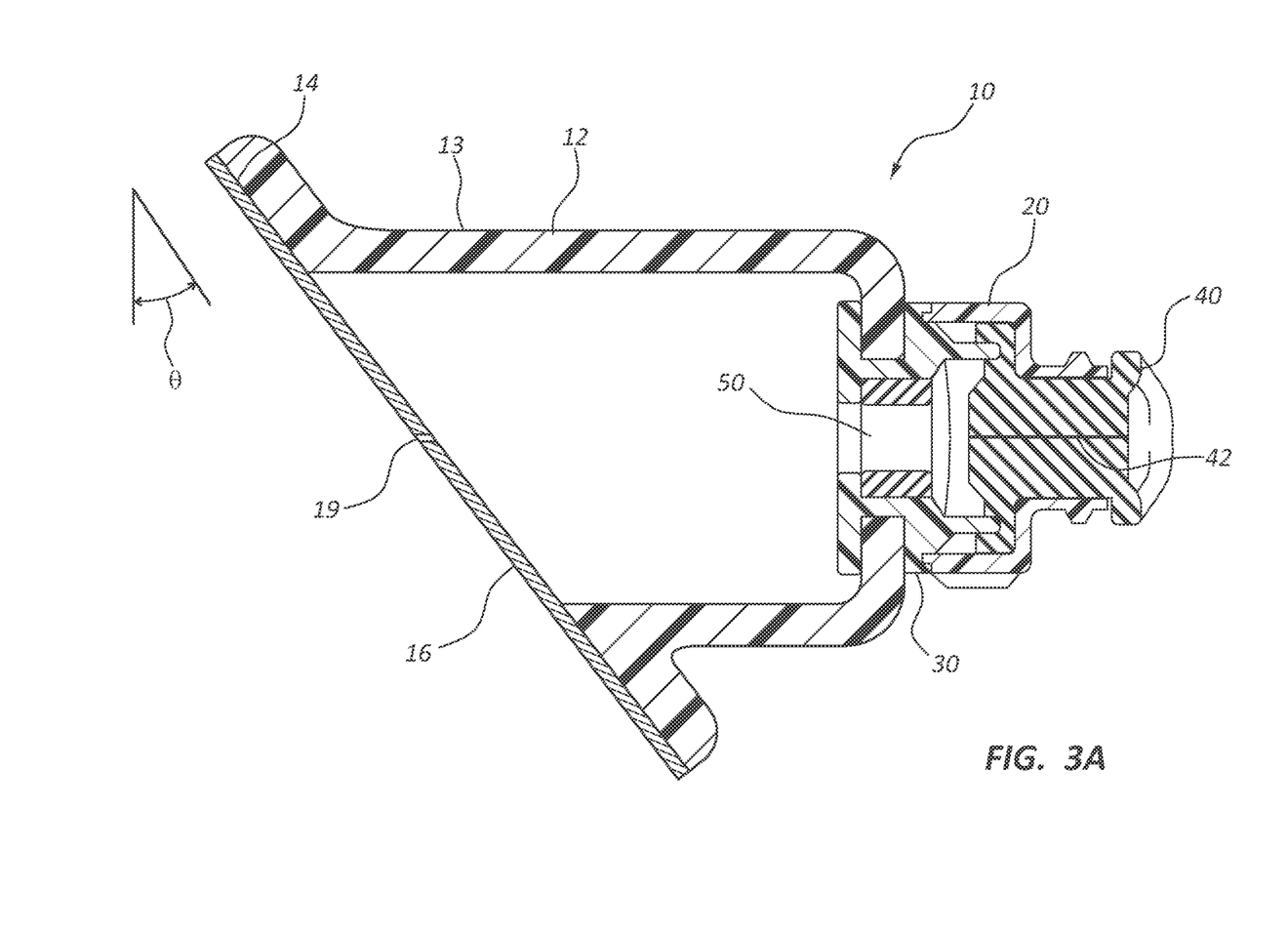
Figure 3B:
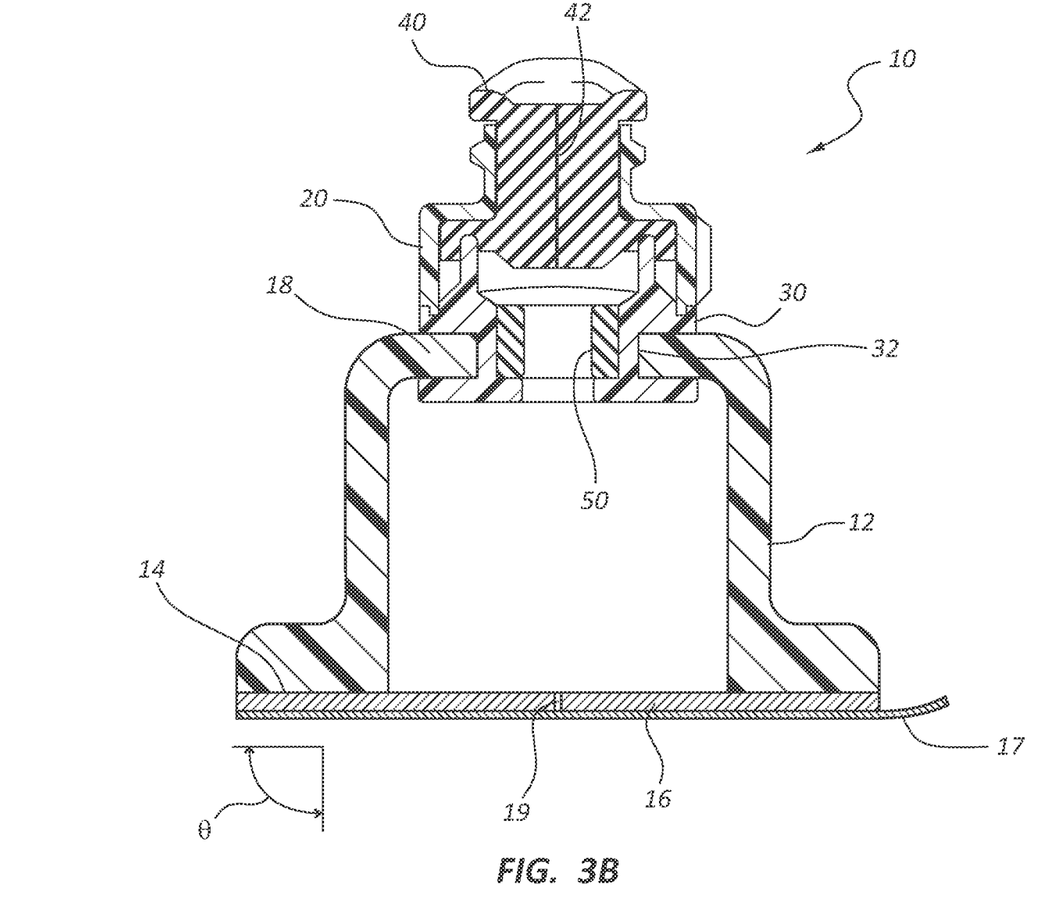

Referring now to FIG. 3A, Luer securement device 10 is shown prior to catheterization. In some embodiments, flexible hood 12 comprises a sidewall 13 and a base 14. In some instances base 14 of flexible hood 12 is angled relative to sidewall 13 to facilitate insertion of the catheter into the patient at a desired angle. The angle of base 14 may be selected based upon an optimal angle of insertion for the catheter. For example, in some embodiments base 14 of hood 12 comprises an angle θ of approximately 30-45°. In other embodiments, angle θ comprises approximately 90°, as shown in FIG. 3B.

Adhesive film 16 may further include a mark or insertion target 19 that is positioned in concentric alignment with wedge seal 50 and slit 42 of septum 40. In some embodiments, insertion target 19 comprises a contrasting color or design that is printed or otherwise provided on film 16. In other embodiments, insertion target 19 comprises a physical hole. Insertion target 19 is useful in accurately positioning Luer securement device 10 onto the patient to achieve catheterization at a desired location. For example, a caregiver might use insertion target 19 to position Luer securement device 10 onto a patient so as to avoid puncturing a mole or hitting a nerve or other anatomical feature of the patient with the needle and catheter. Thus, as the catheter and needle of the catheter inserter are advanced through septum 40 and hood 12, a tip portion of the needle and catheter pass through insertion target 19 and into the desired location of patient 100. In some embodiments, the flexible nature of hood 12 permits slight adjustment of the trajectory the needle and catheter during the catheterization process. Accordingly, the insertion of the needle and catheter is not restricted by insertion target 19. Rather, insertion target 19 may be used as a visual indicator by which to gauge the approximate location of catheterization.

As discussed previously, in some embodiments adhesive film 16 further comprises a protective layer 17 or backing. Protective layer 17 may include any material that is capable of adhering to and being removed from adhesive film 16 without compromising the adhesive properties. For example, in some embodiments protective layer comprises paper having a wax or plastic coating, as is commonly used in the art.

Referring now to FIGS. 4A-4D, a cross section of Luer securement device 10 is shown at various positions during a catheterization procedure. As discussed previously, Luer securement device 10 is used in combination with a catheter inserter 120. Catheter inserter 120 may include any device or combination of devices necessary to deliver and advance catheter 90 through Luer securement device 10 and into a patient. In some embodiments, catheter inserter 120 is configured to advance catheter 90 to a maximum depth of insertion into the patient, wherein the maximum depth of insertion results in base portion 92 being completely seated into wedge seal 50. In other embodiments, hood adapter 30 comprises a physical feature that prevents over-insertion of catheter 90 into the patient.

Figure 4A:
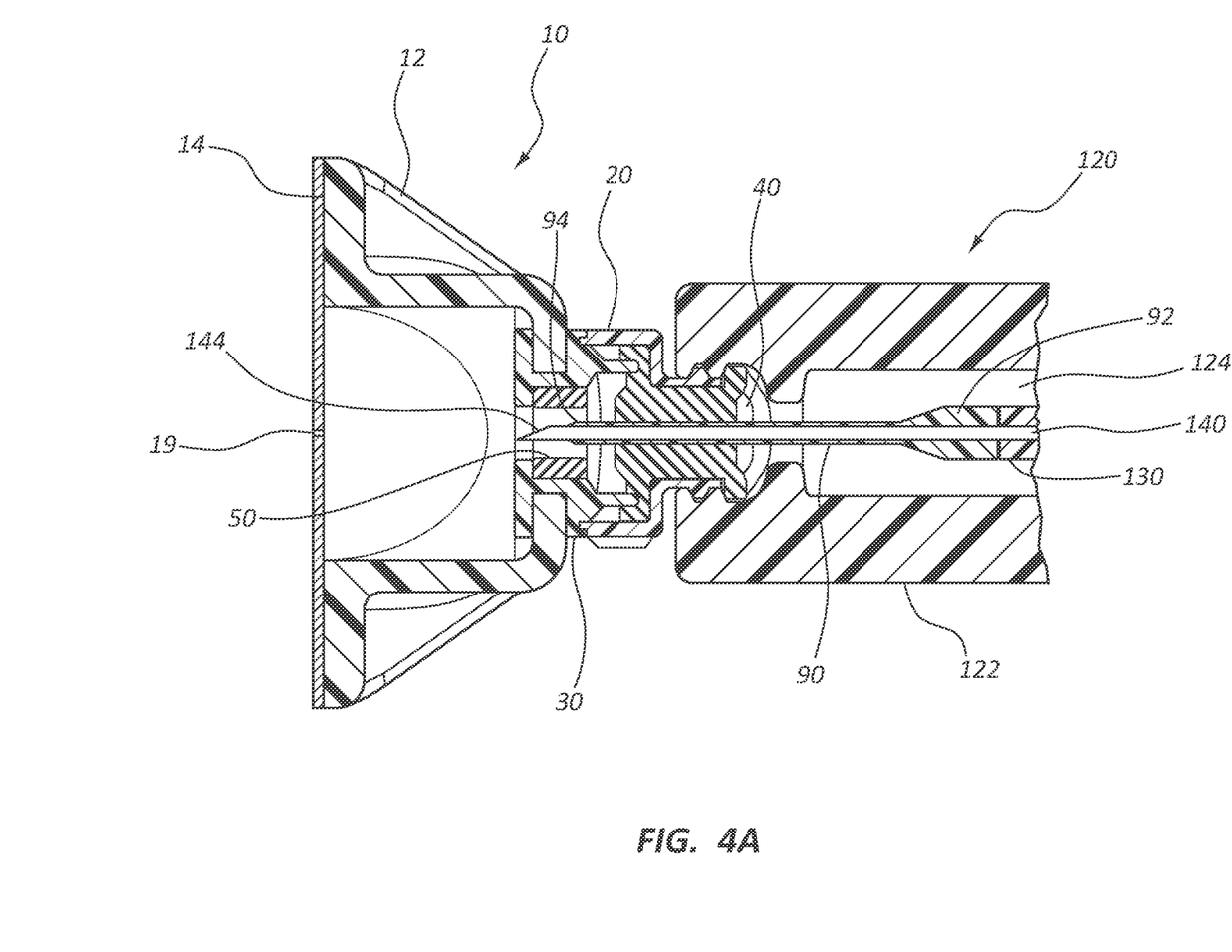

With reference to FIG. 4A, Luer securement device 10 is shown threadedly coupled to catheter inserter 120. In some instances, a catheter inserter 120 is provided having a housing 122 that comprises a set of threads for coupling to Luer securement device 10. Catheter inserter 120 further includes a lumen 124 in which catheter 90 is housed prior to catheterization. A compatible catheter inserter 120 will further include a probe 130 that is configured to advance catheter 90 through lumen 124, through septum 40 and into the patient to a depth at which base 92 of catheter 90 is completely seated in wedge seal 50.

In some instances, catheter 90 comprises a rigid material having a sharpened distal end 94. As such, catheter 90 is capable of being advanced through Luer securement device 10 and into the patient by probe 130. For example, catheter 90 may comprise a metallic or rigid polymer material having a sharpened, beveled distal end 94. In other instances, catheter 90 comprises a flexible or semi-flexible material that is incapable of piercing the patient's skin. Accordingly, in some embodiments a compatible catheter inserter 120 will further comprise a needle 140 that extends through catheter 90, such that a sharpened distal tip 144 of needle 140 is exposed beyond distal tip 94 of catheter 90. During catheterization, sharpened distal tip 144 contacts the patient and provides an opening into which catheter 90 is inserted and advanced. Needle 140 is placed within the lumen of catheter 90 thereby providing rigidity to catheter 90 to facilitate insertion of catheter 90 into the patient.

In some embodiments, the catheterization process beings as catheter inserter 120 is coupled to Luer securement device 10. Probe 130 (or an equivalent variation thereof) advances catheter 90 and needle 140 through septum 40. In some instances, sharpened tip 144 of needle 140 pierces septum 40 to provide a pathway through septum 40. In other instances, septum 40 comprises a self-sealing slit 42 through which sharpened tip 144 and catheter 90 are advanced.

Figure 4B:
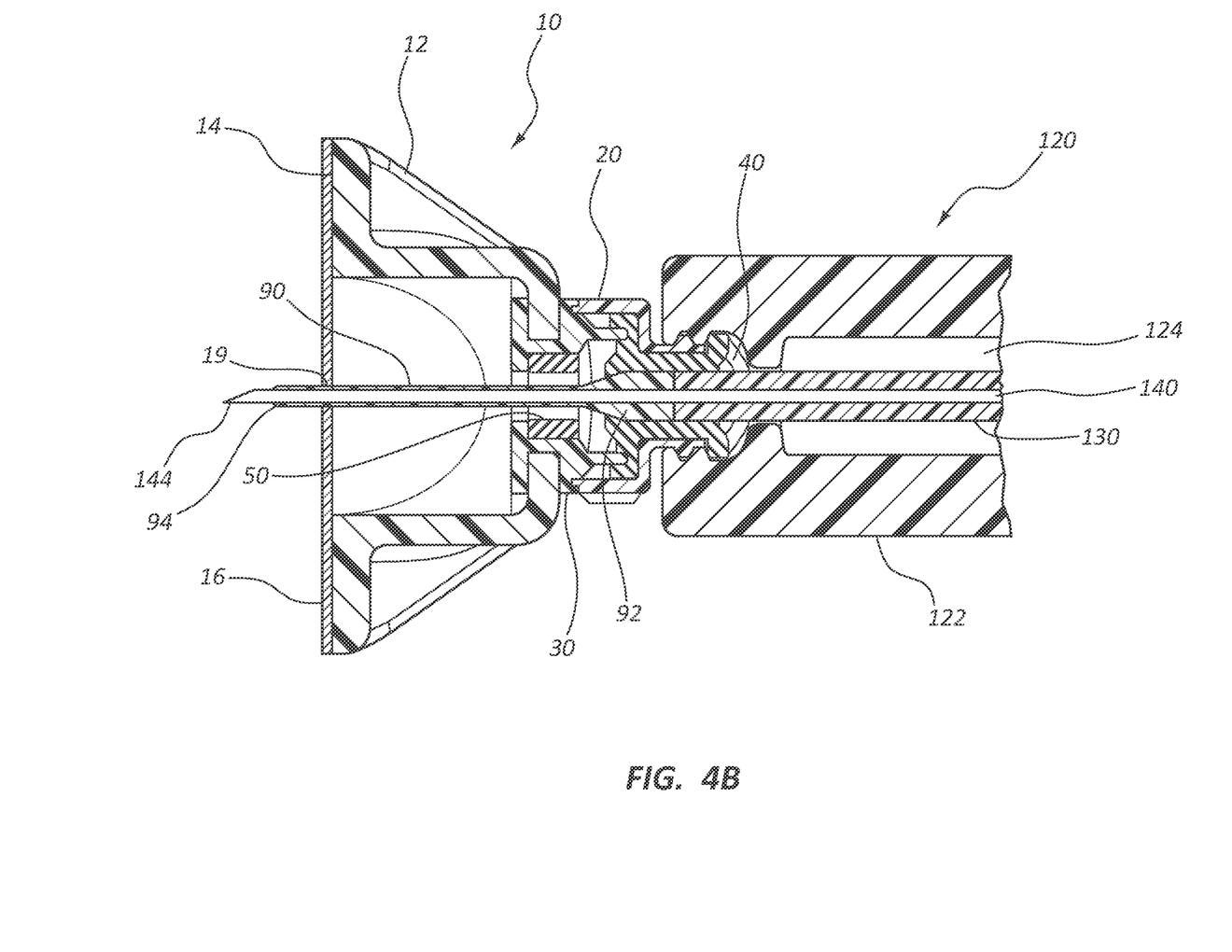
Figure 4C:
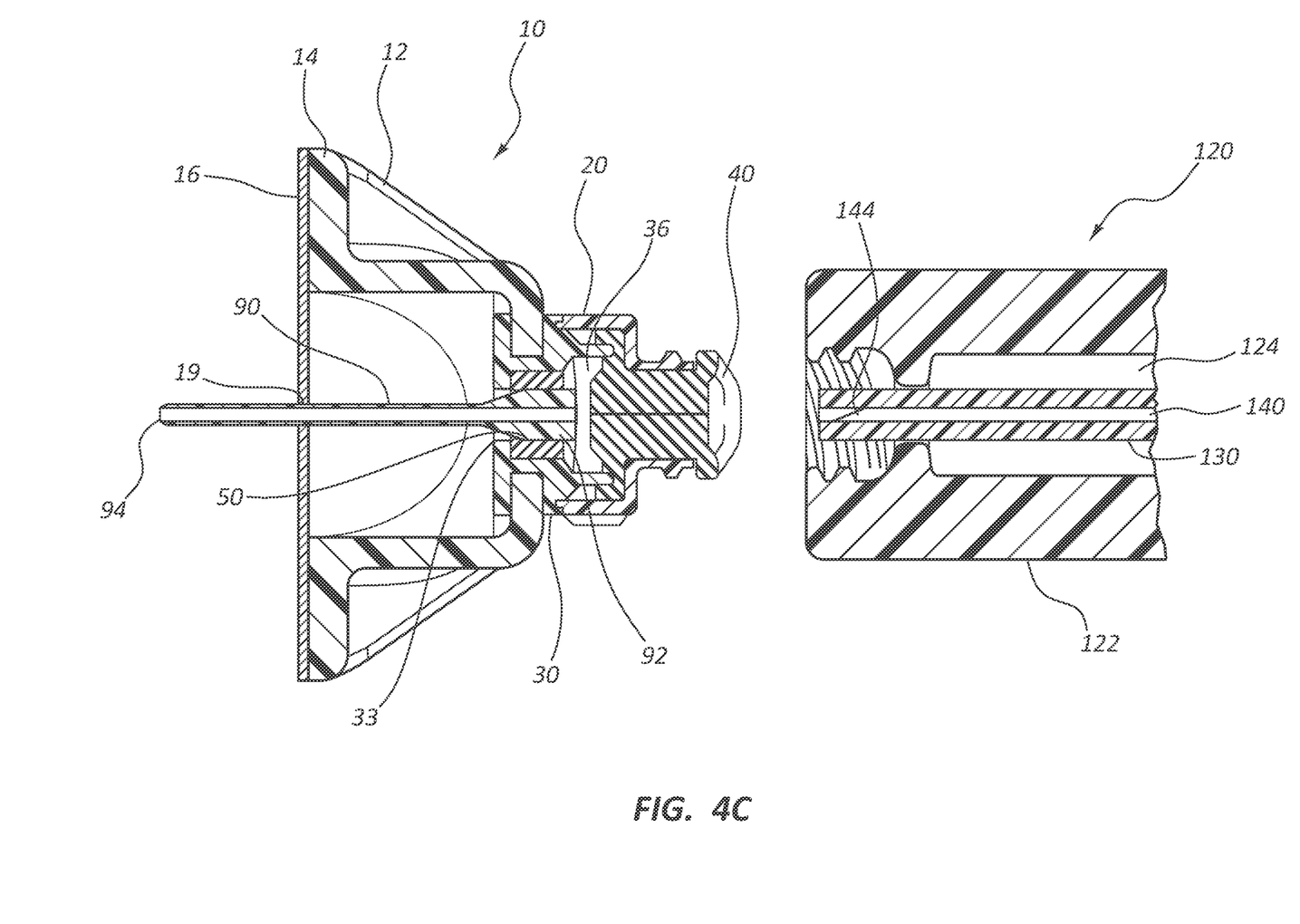

Upon further advancement, sharpened tip 144 pierces adhesive film 16 at approximately insertion target 19, as shown in FIG. 4B. Needle tip 144 and catheter tip 94 are advance through the opening in adhesive film 16 and into the patient until base 92 of catheter 90 is seated into wedge seal 50, as shown in FIG. 4C. In some embodiments, hood adapter 30 comprises a feature which prevents over-insertion of catheter 90 into the patient. For example, in some embodiments aperture 33 comprises a diameter that is less than the outer diameter of base 92. As such, base 92 is prevented from passing through aperture 33. In other embodiments, aperture 33 comprises a chamfered surface that mirrors the tapered surface of base 92. As such, base 92 seats into aperture 33 at a depth where base 92 is fully seated into wedge seal 50.

Following catheterization, catheter inserter 120 is detached from Luer securement device 10. In some embodiments, probe 130 and needle 140 are withdrawn into lumen 124 prior to detaching catheter inserter 120 from Luer securement device 10. Upon withdrawing probe 130 and needle 140 from septum 40, slit 42 self-seals thereby preventing leakage of fluids from catheter 90 and lumen 36.

Figure 4D:
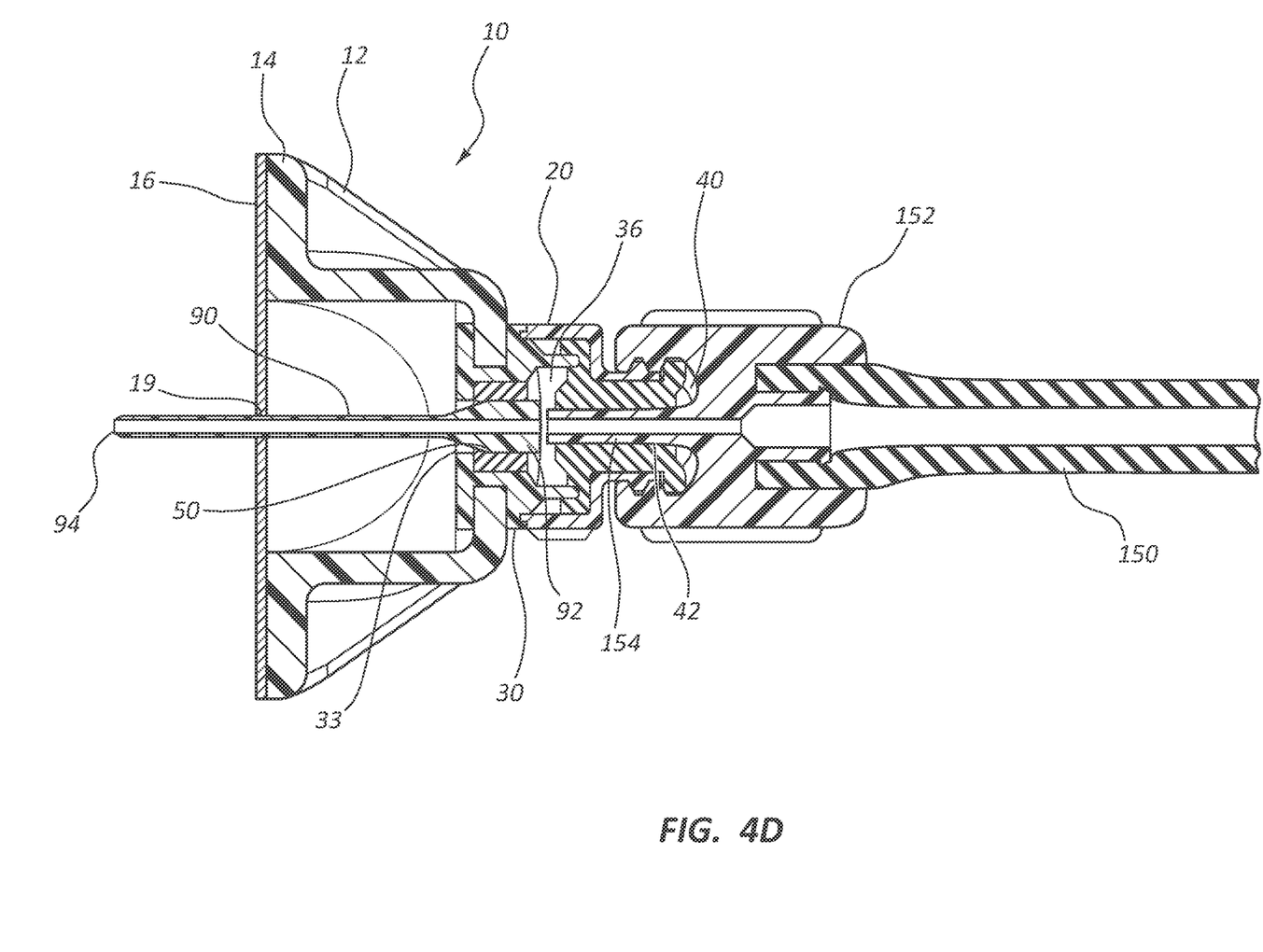

Following removal of catheter inserter 120, Luer securement device 10 may further be coupled to a fluid source, such as a fluid line 150 via a Luer connector 152, as shown in FIG. 4D. In some embodiments, fluid line 150 comprises a probe or nozzle 154 that passed through septum 40 and into lumen 36.

As such, fluid communication between the patient and fluid line 150 is facilitated via catheter 90.

The present invention may be embodied in other specific forms without departing from its structures, methods, or other essential characteristics as broadly described herein and claimed hereinafter. All of the described embodiments and examples are to be considered in any and all respects as illustrative only, and not restrictive. The scope of the invention is, therefore, indicated by the appended claims, rather than by the foregoing description. All changes that come within the meaning and range of equivalency of the claims are to be embraced within their scope.

The invention claimed is:

1. A Luer securement device, comprising:
   a flexible hood comprising a base and a sidewall, the base disposed at a distal end of the flexible hood, the base configured to attach to a surface of a patient, the sidewall extending from the base to a proximal lip portion, the proximal lip portion forming a proximal opening of the flexible hood;
   an adapter comprising a distal portion, a proximal portion, and a lumen that extends through the distal and proximal portions, the distal portion including an exterior annular channel into which the proximal lip portion of the flexible hood inserts to secure the flexible hood to the adapter, the distal portion also including an interior annular channel formed within the lumen, the proximal portion being configured to couple a catheter inserter to the adapter;
   a wedge seal positioned within the interior annular channel, the wedge seal forming an inner lumen within which a proximal base of a catheter is secured when the catheter inserter is employed to insert the catheter into the Luer securement device; and
   a septum secured within the proximal portion of the adapter, the septum sealing a proximal opening of the adapter.

2. The device of claim 1, wherein a distal surface of the base comprises an adhesive film.

3. The device of claim 1, wherein a diameter of the inner lumen of the wedge seal is approximately the same as a diameter of a distal opening of the adapter.

4. The device of claim 1, wherein the wedge seal is formed of a polymer configured to form a fluid seal with the base of the catheter.

5. The device of claim 1, wherein the proximal portion of the adapter comprises external threads for coupling the catheter inserter to the adapter.

6. The device of claim 1, wherein the septum further comprises a self-sealing slit.

7. The device of claim 1, wherein the sidewall is angled relative to the base from about 30° to about 90°.

8. The device of claim 7, wherein the sidewall is angled relative to the base at about 90°.

9. The device of claim 1, wherein a diameter of the lumen is greater in the proximal portion of the adapter than in the distal portion of the adapter.

10. The device of claim 1, wherein a portion of the septum extends out of the proximal opening of the adapter.

11. A method for manufacturing a Luer securement device, comprising:
    providing a flexible hood comprising a base and a sidewall, the base disposed at a distal end of the flexible hood, the base configured to attach to a surface of a patient, the sidewall extending from the base to a proximal lip portion, the proximal lip portion forming a proximal opening of the flexible hood;
    providing an adapter comprising a distal portion, a proximal portion, and a lumen that extends through the distal and proximal portions, the distal portion including an exterior annular channel into which the proximal lip portion of the flexible hood inserts to secure the flexible hood to the adapter, the distal portion also including an interior annular channel formed within the lumen, the proximal portion being configured to couple a catheter inserter to the adapter;
    positioning a wedge seal within the interior annular channel, the wedge seal forming an inner lumen within which a proximal base of a catheter is secured when the catheter inserter is employed to insert the catheter into the Luer securement device; and
    securing a septum within the proximal portion of the adapter, the septum sealing a proximal opening of the adapter.

12. The method of claim 11, further comprising attaching an adhesive film to the base of the flexible hood, the adhesive film enclosing an interior environment of the flexible hood.

13. The method of claim 11, wherein a diameter of the inner lumen of the wedge seal is approximately the same as a diameter of a distal opening of the adapter.

14. The method of claim 11, wherein the wedge seal is formed of a polymer configured to form a fluid seal with the base of the catheter.

15. The method of claim 11, wherein the proximal portion of the adapter comprises external threads for coupling the catheter inserter to the adapter.

16. The method of claim 11, wherein the septum further comprises a self-sealing slit.

17. The method of claim 11, further comprising a step of angling the base relative to the sidewall to an angle from about 30° to about 90°.

18. A Luer securement device, comprising:
    a flexible hood comprising a base and a sidewall, the base disposed at a distal end of the flexible hood, the base configured to attach to a surface of a patient, the sidewall extending from the base to a proximal lip portion, the proximal lip portion forming a proximal opening of the flexible hood;
    an adapter comprising a distal portion, a proximal portion, and a lumen that extends through the distal and proximal portions, the distal portion including an exterior annular channel into which the proximal lip portion of the flexible hood inserts to secure the flexible hood to the adapter, the distal portion also including an interior annular channel formed within the lumen, the proximal portion being configured to couple a catheter inserter to the adapter;
    a wedge seal positioned within the interior annular channel, the wedge seal forming an inner lumen having a first diameter;
    a septum secured within the proximal portion of the adapter, the septum sealing a proximal opening of the adapter; and
    a catheter having a base with an outer diameter substantially equal to the first diameter such that, when the base of the catheter is positioned within the wedge seal, the wedge seal prevents leakage of fluid between the catheter and the wedge seal.

19. The Luer securement device of claim 18, further comprising:
    the catheter inserter, the catheter inserter having a distal portion configured to insert into the adapter and a coupling portion configured to couple to the proximal portion of the adapter, the distal portion having a length configured to position the base of the catheter within the wedge seal when the coupling portion is coupled to the proximal portion of the adapter.

20. The Luer securement device of claim 18, further comprising:
an adhesive film that is secured to a distal surface of the base, the adhesive film covering a distal opening of the flexible hood.

* * * * *